US011485964B2

(12) United States Patent
Peterson et al.

(10) Patent No.: US 11,485,964 B2
(45) Date of Patent: Nov. 1, 2022

(54) COATED CELL CULTURE APPARATUS AND METHODS OF USE

(71) Applicant: Worcester Polytechnic Institute, Worcester, MA (US)

(72) Inventors: Amy Peterson, Cambridge, MA (US); Marsha Rolle, Worcester, MA (US); Ivan Ding, Mays Landing, NJ (US)

(73) Assignee: Worcester Polytechnic Institute, Worcester, MA (US)

( * ) Notice: Subject to any disclaimer, the term of this patent is extended or adjusted under 35 U.S.C. 154(b) by 0 days.

(21) Appl. No.: 16/931,967

(22) Filed: Jul. 17, 2020

(65) Prior Publication Data

US 2021/0171931 A1    Jun. 10, 2021

Related U.S. Application Data

(62) Division of application No. 15/380,374, filed on Dec. 15, 2016, now Pat. No. 10,731,145.

(60) Provisional application No. 62/267,383, filed on Dec. 15, 2015.

(51) Int. Cl.
| | | |
|---|---|---|
| *C12N 13/00* | (2006.01) | |
| *C12M 3/00* | (2006.01) | |
| *C12M 1/00* | (2006.01) | |
| *C12M 1/12* | (2006.01) | |
| *C12N 5/00* | (2006.01) | |

(52) U.S. Cl.
CPC ............. *C12N 13/00* (2013.01); *C12M 21/08* (2013.01); *C12M 23/20* (2013.01); *C12M 25/14* (2013.01); *C12N 5/0068* (2013.01)

(58) Field of Classification Search
CPC ........ C12N 13/00; C12M 21/08; C12M 23/20
See application file for complete search history.

(56) References Cited

PUBLICATIONS

Peterson et al., pH-Controlled Release of Proteins from Polyelectrolyte-Modified Anodized Titanium Surfaces for Implant Applications, Sep. 2012, BioMacromolecules, No. 13, pp. 120-3126 (Year: 2012).*
Peterson et al., Growth Factor Release from Polyelectrolyte-Coated Titanium for Implant Applications, Dec. 2013, Applied Materials and Interfaces, No. 6, pp. 1866-1871 (Year: 2013).*
Sundermann et al., Bone Morphogenic Protein 2 (BMP-2) Aggregates Can be Solubilized by Albumin-Investigation of BMP-2 Aggregation by Light Scattering, Nov. 2020, Pharmaceutics, No. 12, pp. 1-20 (Year: 2020).*

* cited by examiner

*Primary Examiner* — Dah-Wei D. Yuan
*Assistant Examiner* — Andrew J Bowman
(74) *Attorney, Agent, or Firm* — Greenberg Traurig, LLP; Roman Fayerberg (57) ABSTRACT

Device, and methods of using or making the device, for engineering cells in vitro are disclosed. In some aspects, a cell culture device comprises at least one glass or polymer surface configured for incubating cells in a culture medium; a charged molecule electrostatically bound to the surface; and a polyelectrolyte multilayer (PEM) electrostatically bound to the charged molecule, the PEM comprising one or more bi-layers of oppositely charged polyelectrolytes, and the PEM having a sufficient thickness to permit release of the charged molecule into the culture medium in a controlled released manner.

20 Claims, 10 Drawing Sheets

COATED CELL CULTURE APPARATUS AND METHODS OF USE

RELATED APPLICATIONS

This application is a divisional patent application of U.S. application Ser. No. 15/380,374, filed Dec. 15, 2016, which claims the benefit of and priority to U.S. Provisional Application No. 62/267,383, filed on Dec. 15, 2015, and which is incorporated herein by reference in its entirety.

STATEMENT OF GOVERNMENT SUPPORT

This invention was made with Government Support under Grant Number ECC-1156821 awarded by the National Science Foundation. The Government has certain rights in the invention.

BACKGROUND

1. Field

The present disclosure is directed to a device, and methods of making or using the device, for engineering cells via controlled release of an agent into a tissue culture medium, and more particular, where the controlled release is mediated by a polyelectrolyte multilayer (PEM) overlaying the agent.

2. Background

Cell culture is the process by which cells are grown under controlled conditions, generally outside of their natural environment. A growth medium or culture medium is a liquid or gel designed to support the growth of cells. Animal cells in culture are often grown on a flat surface to which they attach, and the medium is usually provided in a liquid form, which covers the cells and may contain essential amino acids, salts, minerals, and carbohydrates. Components of growth media used for cell culture are derived from whole organisms, and cells grown in culture often cannot grow without the addition of, for instance, hormones or growth factors which usually occur in vivo. Manual addition of complex growth factor mixtures, concentrations and timing may contribute to batch-to-batch inconsistencies in cultured cell lots, loss of phenotype, and add cost to cell expansion, scale up and manufacturing. Reduction in sources of variation and inconsistency in cell culture would improve yield and efficacy of the resulting manufactured cells. Control over timing of release will allow tailoring of the cell culture surface to the desired application.

There is still a need for devices and methods that would enable release of additives into cell culture at a controlled, consistent rate.

SUMMARY

The present disclosure is directed to a cell culture device for advancing in vitro cell and tissue engineering.

In some aspects, the present disclosure provides a cell culture device comprising at least one glass or polymer surface configured for incubating cells in a culture medium; a charged molecule electrostatically bound to the surface; and a polyelectrolyte multilayer (PEM) electrostatically bound to the charged molecule, the PEM comprising one or more bi-layers of oppositely charged polyelectrolytes, and the PEM having a sufficient thickness to permit release of the charged molecule into the culture medium in a controlled released manner.

In some aspects, the present disclosure provides a method of engineering cells comprising incubating cells in a cell culture device comprising: at least one glass or polymer surface configured for incubating cells in a culture medium; a charged molecule electrostatically bound to the surface; and a polyelectrolyte multilayer (PEM) electrostatically bound to the charged molecule, the PEM comprising one or more bi-layers of oppositely charged polyelectrolytes, and the PEM having a sufficient thickness to permit release of the charged molecule into the culture medium in a controlled released manner; allowing the charged molecule to be released from the PEM in the controlled release manner, the charged molecule having a measurable and desired effect on the cells; monitoring the cells for the measurable and desired effect; and harvesting cells demonstrating the measurable and desired effect.

In some aspects, the present disclosure provides a method of preparing a device for tissue engineering comprising: coating at least a portion of a glass or polymer surface of a device configured for incubating cells in a culture medium with a charged molecule; and depositing a polyelectrolyte multilayer (PEM) on top of the charged molecule, the PEM comprising one or more bi-layers of oppositely charged a polyanion and polycation; adjusting a pH of the polyanion and polycation to enable a desired rate of release of the charged molecule.

In some embodiments, the surface is negatively charged or is hydrophilic. In some embodiments, the charged molecule includes a positively charged portion. In some embodiments, the charged molecule is a growth factor. In some embodiments, the PEM comprises between 3 and 10 bi-layers of oppositely charged polyelectrolytes. In some embodiments, the PEM is a combination of poly(methacrylic acid) (PMAA) and poly-L-histidine (PLH). In some embodiments, the PEM comprises a combination of a polyanion and polycation that has a closed state with a pH range of 1 to 2 units. In some embodiments, the PEM comprises a combination of a polyanion and polycation that has a closed state at pH between 6.5 and 8.

BRIEF DESCRIPTION OF THE DRAWINGS

The present disclosure is further described in the detailed description which follows, in reference to the noted plurality of drawings by way of non-limiting examples of exemplary embodiments, in which like reference numerals represent similar parts throughout the several views of the drawings, and wherein.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

The following description provides exemplary embodiments only, and is not intended to limit the scope, applicability, or configuration of the disclosure. Rather, the following description of the exemplary embodiments will provide those skilled in the art with an enabling description for implementing one or more exemplary embodiments. It will be understood that various changes may be made in the function and arrangement of elements without departing from the spirit and scope of the disclosure as set forth in the appended claims.

Tissue culture is often done in cell culture devices such as dishes or flasks. In some embodiments, the flasks may be plastic or glass, and the tissue culture may be done statically or dynamically (i.e., roller bottle or bioreactor chamber). Tissue engineering may require addition of a growth factor (or any agent capable of altering the features of cells) to a population of cells, where the growth factor (or agent) is exogenously supplied to the cells. Growth factors may be applied to drive proliferation, differentiation, or maintenance of stem cell pluripotency, depending on the cell type in culture and desired effect of growth factor release. For example, expansion of a therapeutic cell type is desired to generate large numbers of cells to manufacture engineered tissues, or for transplantation to injured tissues for regenerative medicine applications. Examples include (but are not limited to) expansion of skeletal muscle progenitor cells (or satellite cells), which require constant application of FGF-2; application of PDGF and TGFβ1 to drive proliferation of vascular smooth muscle cells, and VEGF to drive proliferation of endothelial cells. Constant application of growth factors and cytokines can also expand stem cells while maintaining stem cell pluripotency (e.g., addition of FGF-2 to human embryonic stem cell cultures, and LIF-1 to mouse embryonic stem cells). These and other factors have been identified as mediators of pluripotency that can be added exogenously to culture medium, are required to maintain stem cell pluripotency and are normally provided by feeder cells or feeder cell-conditioned medium, which can introduce lot to lot variability to the cultures that would be alleviated by a controlled release culture surface. Growth factors can also be used to drive differentiation into defined cell types from pluripotent stem cells, such as the addition of BMPs to mesenchymal stem cells to drive osteoblast differentiation. Proliferation, differentiation, and pluripotency are indicated by each cell type in each application by expression of genes, proteins, and cellular morphologies phenotypes or functions that can be measured to assess the effects of growth factor release from PEMs compared to repeated addition of growth factors to the culture medium.

In some embodiments of the present disclosure, a cell culture device comprises at least one surface configured for incubating cells in a culture medium, a charged molecule electrostatically bound to the surface, and a polyelectrolyte multilayer (PEM) electrostatically bound to the charged molecule, the PEM comprising a plurality of oppositely charged layers of polyelectrolytes, and the PEM having a sufficient thickness to permit release of the charged molecule into the culture medium in a controlled released manner.

In some embodiments, a method of engineering cells comprises incubating cells in a device, releasing the charged molecule from the PEM in the controlled release manner, the charged molecule having a measurable and desired effect on the cells, monitoring the cells for the measurable and desired effect, and harvesting cells demonstrating the measurable and desired effect. The device comprises an interior surface configured for incubating the cells in a culture medium, a charged molecule electrostatically bound to the surface, and a polyelectrolyte multilayer (PEM) electrostatically bound to the charged molecule, the PEM comprising a plurality of oppositely charged layers of polyelectrolytes, and the PEM having a sufficient thickness to permit release of the charged molecule into the culture medium in a controlled released manner.

In some embodiments, a method of preparing a device for tissue engineering comprises coating at least a portion of a surface of a device configured for incubating cells in a culture medium with a charged molecule, and forming a polyelectrolyte multilayer (PEM) on top of the charged molecule, the PEM comprising a plurality of oppositely charged layers of polyelectrolytes. The forming step comprises electrostatically binding a first charged electrolyte to the charged molecule to form a first polyelectrolyte layer, the first charged electrolyte being either a polyanion or a polycation, washing the interior surface, drying the interior surface, electrostatically binding a second charged electrolyte to the first charged electrolyte to form a second polyelectrolyte layer, the second charged electrolyte being of an opposite charge from the first charged electrolyte, and repeating the washing, drying and electrostatically binding steps until the PEM is of a sufficient thickness to permit release of the charged molecule into the culture medium in a controlled release manner. In some aspects, a method for modulating a release of a charged molecule is provided. In some aspects, a method of adsorbing a charged molecule on a substrate surface is disclosed. In some aspects, a method for cleaning a substrate for re-use is provided.

Figure 1:
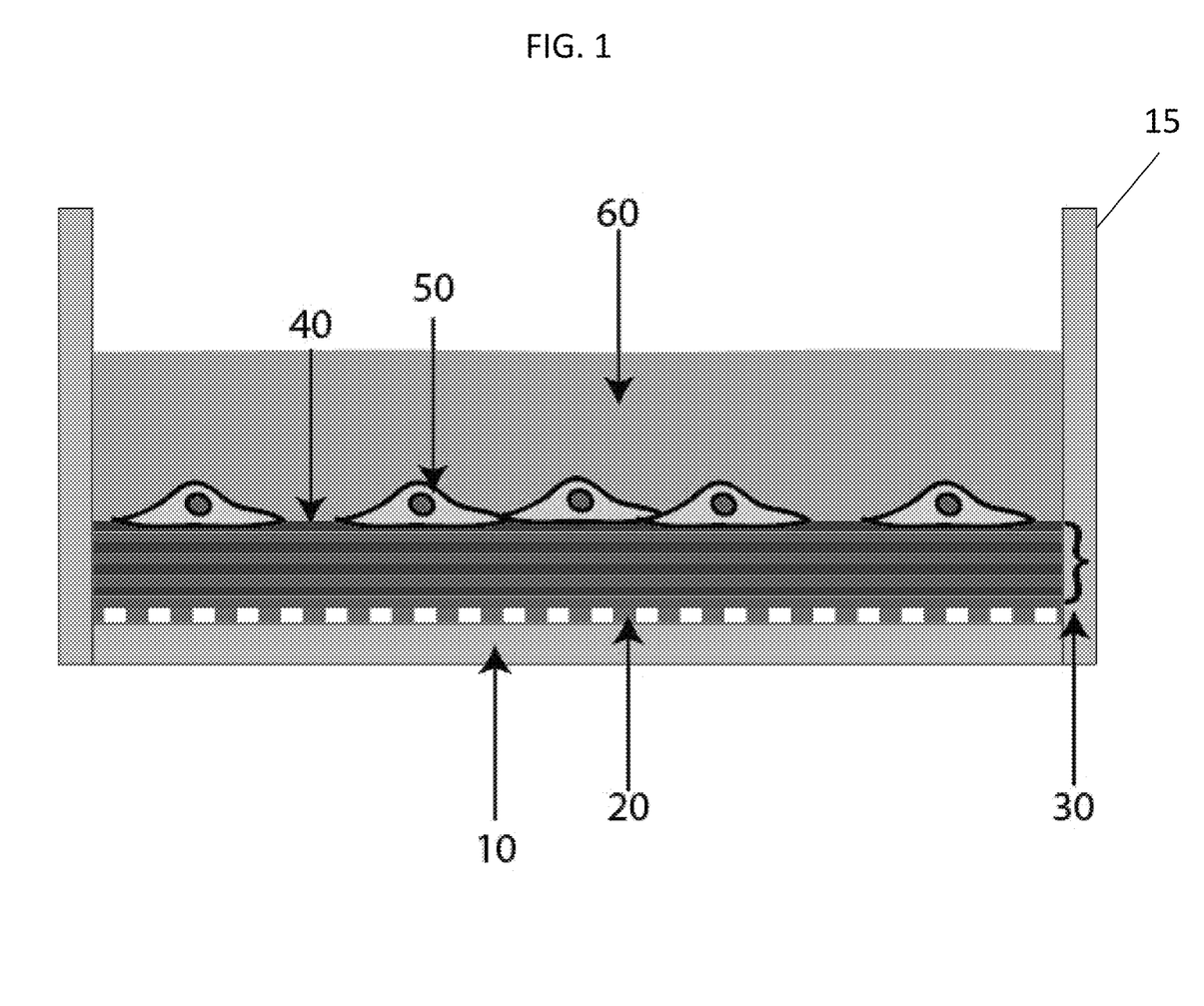
FIG. 1 illustrates one embodiment of a cell culture device of the present disclosure.

In reference to FIG. 1, the present disclosure provides coated cell culture devices and methods of use of such devices for controlling release of charged molecules into a tissue culture medium. In some embodiments, there is provided a cell culture device 15 that can be used for in vitro tissue engineering within the cell culture device without having to exogenously supply any reagents or growth factors. In some embodiments, a substrate 10 (such as a surface of the cell culture device 15) may be coated with one or more layers of charged molecules 20, followed by a layer of Polyelectrolyte Multilayer (PEM) 30, which can include one or more individual layers. In operation, cells 50 can be adhered to the top layer 40 of the PEM 30 and are cultured in a culture or growth medium 60. The PEM layer 30 may allow for release of the charged molecule 20 into the cell culture in a controlled manner.

Substrates

In some embodiments, glass or plastic substrates may be employed for the coatings of the present disclosure. In some embodiments, such glass or plastic substrates may form a surface of a cell culture device, for example, a Petri dish or a flask. In some embodiments, the substrates may be planar or 2 dimensional. In some embodiments, the substrates may have a 3 dimensional pattern. In some embodiments, the substrates may have a hydrophilic surface or a negatively charged surface. In some embodiments, substrate surfaces can be improved through increased roughness to increase actual surface area. In some embodiments, surfaces can also be improved through chemical/plasma treatment to increase the number of hydroxyl or other negatively charged groups.

In some embodiments, substrates may be cylindrical (such as a hollow fiber or roller flask), spherical (such as a microcarrier bead), or flat. The topography of flat or curved surfaces may be engineered with repeating patterns such as grooves, pillars, or platforms. In some embodiments, the substrates may include parallel grooves that induce cell alignment. In some embodiments, the substrates may include discrete pillars or islands to control cell adhesion contact area or to spatially control the release of charged molecules. Because the coatings of the present disclosure are conformable, the coating of the present disclosure may assume the shape and features of the underlying substrate.

By carefully selecting the type or types of polymer, the chemical and physical properties of the polymer can be highly tailored to adsorb specific proteins and cells for a particular application. In some embodiments, the substrate surface is negatively charged or is hydrophilic.

Charged Molecules

In some embodiments, the charged molecules may be adsorbed on the substrate surface through electrostatic interactions. In some embodiments, the charged molecule is positively charged. In some embodiments, the charged molecule is a zwitterionic molecule.

In some embodiments, if the substrate surface is uncharged, charged molecule with isoelectric points (IEP) greater than 9 may be adsorbed. In some embodiments, a charged molecule having IEP greater than 7 can be employed on a hydrophilic surface.

The amount of adsorption that can occur can depend on the charge difference (greater charge difference, greater amount of adsorption). Typically, glass (silica) has a larger zeta potential than titanium dioxide. In some embodiments, the amount of the charged molecule adsorbed may be changing the concentration of the charged molecule in the solution applied to the substrate surface. In some embodiments, the concentration of the charged molecule in the solution to be applied on the +substrate surface may range from between about 0.0125 mg/ml to about 0.1 mg/ml. In some embodiments, the adsorption time can be changed to change the amount of adsorption. In some embodiments, the adsorption time can range between about 5 minutes and about 10 minutes, however, longer times may be needed for surfaces with less charge.

In some embodiments, the charged molecules may be applied in multiple layers. In some embodiments, the IEPs of the layers can differ by at least 2 pH units. In some embodiments, the charged molecule comprises a mixture of multiple charged molecules. In some embodiments, the IEPs of the individual charged molecules in the mixture can differ by at least 2 pH units.

In some embodiments, the charged molecule is a protein, a peptide, a nucleic acid, or an antibody. In some embodiments, the nucleic acid is an RNA or DNA. In some embodiments, the RNA is an miRNA or an siRNA. In some embodiments, the DNA may be genomic DNA, synthetic DNA, plasmid DNA, cDNA, or a vector for delivery of any one of genes, DNA or RNA. In some embodiments, the protein is a growth factor, a peptidomimetic, a cytokine, a protease or a transcription factor. In some embodiments, the peptide is a short peptide of from about 2 to about 100 amino acids in length. In some embodiments, the peptide is a protein fragment. In some embodiments, the protein may be a transcription factor, such as HIF-1α. In some embodiments, the protein may be a protease, such as MMP-2.

Growth factors are proteins that stimulate cellular functions including proliferation, differentiation, and growth. In some embodiments, the growth factor(s) may lead to a desirable and measurable effect on cultured cells, in particular when the cells are exposed to the growth factors in a controlled release manner. In some embodiments, the growth factor acts as a signalling molecule. Growth factors are also considered to be morphogens, which are biomolecules that act as spatial regulators. Through concentration gradients, they dictate cell behavior and tissue development. Morphogen gradients can cause cell migration, the expression of different genes, and the development of different tissues. Each growth factor has specific functions that depend on type and location in tan organism. Often, growth factors are grouped into families. Growth factors within a family have similar functions and often have similar structures. Growth factors are synthesized naturally by an organism; additionally, recombinant forms of growth factors can be synthesized in the laboratory by combining specific sections or domains of different proteins. As examples of growth factors that may be incorporated in films according to the invention are activins (such as activin A), angiopoietins, bone morphogenetic proteins (BMP), epidermal growth factors (EGF), ephrins, erythropoietin (EPO), fibroblast growth factors (FGF), granulocyte-colony stimulating factor (G-CSF), granulocyte-macrophage colony stimulating factor (GM-CSF), growth differentiation factor-9 (GDF-9), hepatocyte growth factor (HGF), hepatoma derived growth factor (HDGF), hypoxia-inducible factors (HIF), insulin, insulin-like growth factor (IGF), interleukins, keratinocyte growth factor (KGF), leukemia inhibitory factor (LIF), myostatin (GDF-8), nerve growth factor (NGF) and other neurotrophins, platelet-derived growth factor (PDGF), stromal cell-derived factor-1 (SDF-1), thrombopoietin (TPO), transforming growth factors (TGF), tumor necrosis factor (TNF), and vascular endothelial growth factor (VEGF). In some embodiments, the growth factor may be a BMP such as BMP-2 or BMP-9. In some embodiments, the growth factor may be TGF-β1, FGF-2/bFGF.

Polyelectrolyte Multilayers (PEM).

Polyelectrolytes are polymers that include ionically dissociable groups. Polyelectrolytes can have positively (polycation) or negatively (polyanion) charged repeat units or positively and negatively charged repeat units (polyampholytes). Ions on strong polyelectrolytes are completely dissociable, whereas dissociation is pH-dependent in the case of weak polyelectrolytes. Polyelectrolytes of the present disclosure are biocompatible and also biodegradable.

Figure 2A:
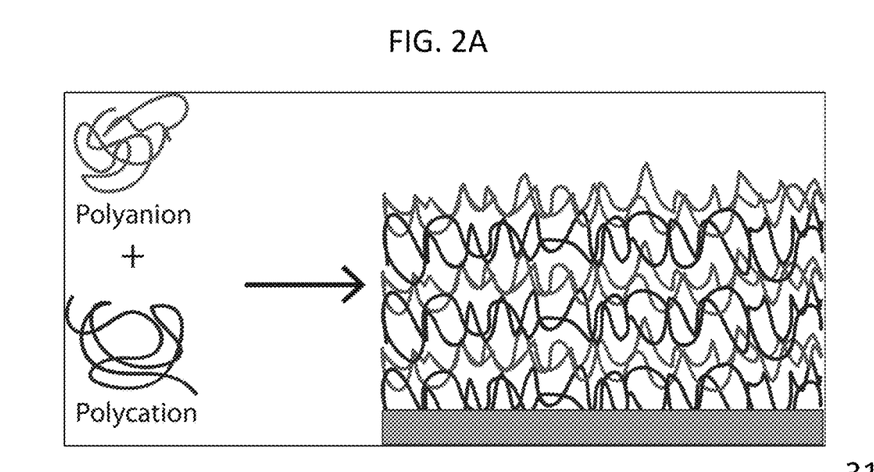
FIG. 2A is a model representation of a polyelectrolyte multilayer (PEM)
Figure 2B:
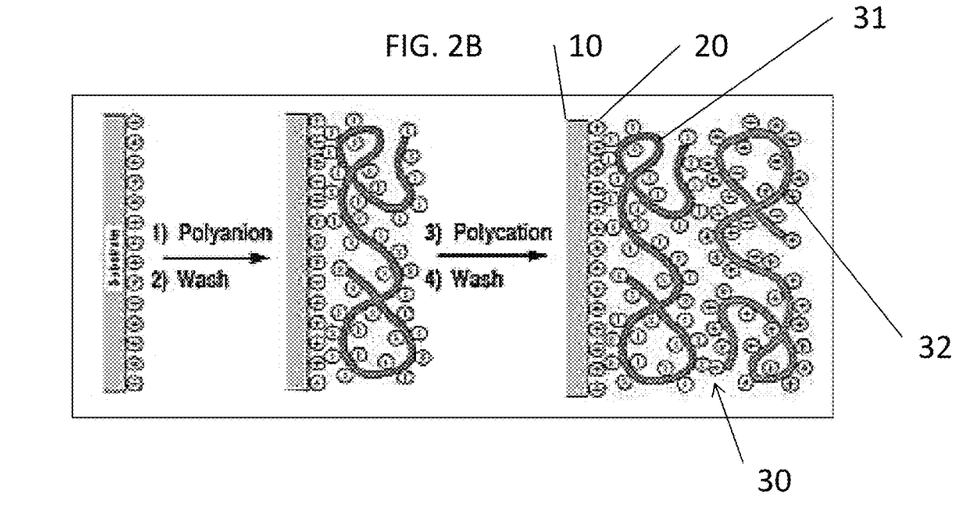
FIG. 2B illustrates a PEM formed on top of a charged molecule bound to a surface.

Polyelectrolyte multilayers include a combination of positively and negatively charged polyelectrolytes. In reference to FIGS. 2A and 2B, in some embodiments, PEMs are formed by depositing polycations 32 and polyanions 31 on top of a layer of charged molecule 20 adsorbed on the surface 10. In some embodiments, the polycations 32 and polyanions 31 can be deposited in an alternative fashion as shown in FIG. 2B.

In some embodiments, the PEMs of the present disclosure comprise a combination of a weak polyanion and weak polycation. In some embodiments, the PEMs of the present disclosure include a weak polyanion or a weak polycation. In some embodiments, whether a polyanion or a polycation is coated on top of the charge molecule layer may depend on a IEP of the charged molecule layer. For example, in some embodiments, if the IEP of the charged molecule layer is greater than 7, then the first PEM layer can be a polyanion, while if the IEP of the first layer is less than 7, then the first PEM layer can be a polycation.

In some embodiments, the coatings of the present disclosure may include one or more bilayers of PEM, with each bilayer comprising one polycation layer and one polyanion layer. In some embodiments, the layer of PEM may include from about 2 bi-layers to about 100 bi-layers. In some embodiments, the sufficient thickness of PEM is from about 5 bi-layers to about 10 bi-layers. In some embodiments, the thickness of PEM is from about 3 to about 10 bi-layers.

In some embodiments, the polyelectrolytes may include, but are not limited to, poly(methacrylic acid) (PMAA); poly-L-histidine (PLH); poly(styrene sulfonate) (PSS); poly-L-lysine (PLL); poly(acrylic acid) (PAA); poly(diallyl dimethyl ammonium chloride) (PDADMAC); polyethyleneimine (PEI); poly(allylamine hydrochloride) (PAH), and similar polyelectrolytes. In some embodiments, the polyanions may be poly(acrylic acid), poly(methacrylic acid), or poly(sodium 4-styrene sulfonate). In some embodiments, the polycations may be poly-1-histidine, poly-1-lysine, poly (diallyldimethylammonium chloride), polyethylene imine, or polyallylamine hydrochloride. In some embodiments, the PEM combinations may include PMAA/PLH; PSS/PLH; PMAA/PLL; PAA/PLH; PAA/PLL; PSS/PLL; PMAA/PDADMAC; PAA/PDADMAC; PMAA/PEI; PSS/PEI; PAA/PEI; PMAA/PAH; PAA/PAH; PSS/PAH; PAA/Chitosan; PMAA/Chitosan; and PSS/Chitosan.

In some embodiments, weak polycations and/or polyanions are deposited on a surface in an alternating fashion, only one of which needs to be weak. In some embodiments, a strong polyelectrolyte is a polyelectrolyte in which the ions are completely dissociable. In some embodiments, a weak polyelectrolyte is a polyelectrolyte in which ion dissociation is pH dependent. In some embodiments, the weak/strong transition is when dissociation constants ($K_a$ or $K_b$) are 50-100, with higher dissociation constants denoting a strong ion pair and lower dissociation constants denoting a weak ion pair. For example, weak polyelectrolytes may include, but are not limited, to PLH, PAH, PAA, PMAA, PEI, PLL. Strong polyelectrolytes may include, but are not limited to, PDADMAC, PSS.

In some embodiments, the PEM includes at least one weak polyelectrolyte for the PEM to exhibit a pH-sensitive response (i.e. positive-negative-positive ordering of charge in the layers, or vice versa). Electrostatic interactions can then form a pH-sensitive PEM film that exhibits a "closed" state when the opposing charges of the polyelectrolytes neutralize each other, but an "open" state when the environment provides additional charges to neutralize either the polyanion or polycation. Polyanions and polycations in polyelectrolyte films produced in a layer-by-layer fashion can be highly entangled with each other, which allows for closing and opening of films several times. In the closed state, diffusion (release) is slower or even completely prevented, but in the open state, diffusion or release are more rapid. The pH ranges that result in a closed or open state are individual to a given polyanion and polycation pair. For example, the table below shows closed state pH ranges for different combinations of polyanions and polycations.

|  | PAA | PMAA |
|---|---|---|
| Chitosan | 2.8-4.8 | 3.5-7.5 |
| PAH | 2.2-7.5 | 3.3-9.4 |
| PEI | 7.0-10.6 | 7.5-10.6 |
| PLH | 2.2-9.1 | 5.7-7.7 |
| PLL | 2.9-4.8 | 5.2-10.8 |

Outside these ranges the combination shown above will exist in an open state.

In some embodiments, PEM formation has been shown to be an entropy-driven process through the release of counterions that are no longer restricted to the polyelectrolyte surface. Coulombic interactions between oppositely charged polyelectrolytes lead to interpolymer ionic condensation. Hydrogen bonding, van der Waals forces, hydrophobic interactions, and dipole interactions are non-Coulombic interactions that are also involved in PEM formation.

The properties of a PEM are dependent upon many processing parameters including polyelectrolyte pair, molecular weight, deposition pH, salt/electrolyte concentration, and number of layers. In some embodiments, the properties of a PEM can be tailored precisely for a given application. For example, in some embodiments, the PEM properties can depend a desired amount of growth factor in the media, and, optionally, on the optimal roughness or surface energy of the substrate. For example, 4 ng/mL of FGF2 is a physiological concentration for certain systems. This can be achieved over short periods of time on a tissue culture plastic surface with an initial FGF2 solution concentration of 0.1 mg/mL for a $(PLH/PMAA)_5$ PEM assembled at pH=4. However, this time can be increased by increasing the initial solution concentration of FGF2 to increase the amount of available FGF2, increasing the roughness of the substrate, and/or combining this with a PEM that is more closed, for example $(PLH/PMAA)_5$ assembled at pH=5-8, or $(PLH/PMAA)_{10}$ assembled at pH=4.

In some embodiments, the PEM includes a combination of a polyanion and polycation that has a closed state with a pH range of about 1 to about 3 units. In some embodiments, the PEM includes a combination of a polyanion and polycation that has a closed state with a pH range of about 1 to about 2 units. That is, the PEM combination transitions from a closed state to an open state over between about 1 to about 2 units of pH. Such combination may allow for tailoring the PEM for a desired release rate. In some embodiments, the PEM includes a combination of a polyanion and polycation that has a closed state at pH between about 6.5 and about 8. In some embodiments, the PEM includes a combination of a polyanion and polycation that has a closed state at pH between about 7 and about 8.

In some embodiments, post-processing can change PEM properties. For example, annealing of a PEM to the surface in a high concentration salt solution results in significant smoothing of the surface. The presence of salt enhances the amount of polyelectrolyte diffusion because salt ions will condense on polyelectrolytes, breaking PEC bonds and allowing polyelectrolytes to form new bonds.

A number of methodologies are available for characterizing PEMs. In some embodiments, the methodologies may comprise ellipsometry (thickness), quartz crystal microbalance with dissipation monitoring (mass adsorbed, viscoelasticity), contact angle analysis (surface energy), Fourier transform infrared spectroscopy (functional groups), X-ray photoelectron spectroscopy (chemical composition), scanning electron microscopy (surface structure), and atomic force microscopy (roughness/surface structure).

PEM Formation/Processing

An additional parameter that can affect the properties of a PEM is the processing mechanism. In some embodiments, PEMs may be deposited by pipetting polyanion or polycation solutions into/onto the dish, either as a mixture or sequentially. In some embodiment, the solution pH of both polyanion and polycation is adjusted to the same pH value, which may aid in both modulating the release and maintaining bioactivity of charged molecule, such as growth factors.

In some embodiments PEMs can be formed on the surface or on top of a charged molecule that is bound to the surface by dip coating the surface into a PE solution. In some embodiments, spray coating and spin coating may be used.

Figure 3:
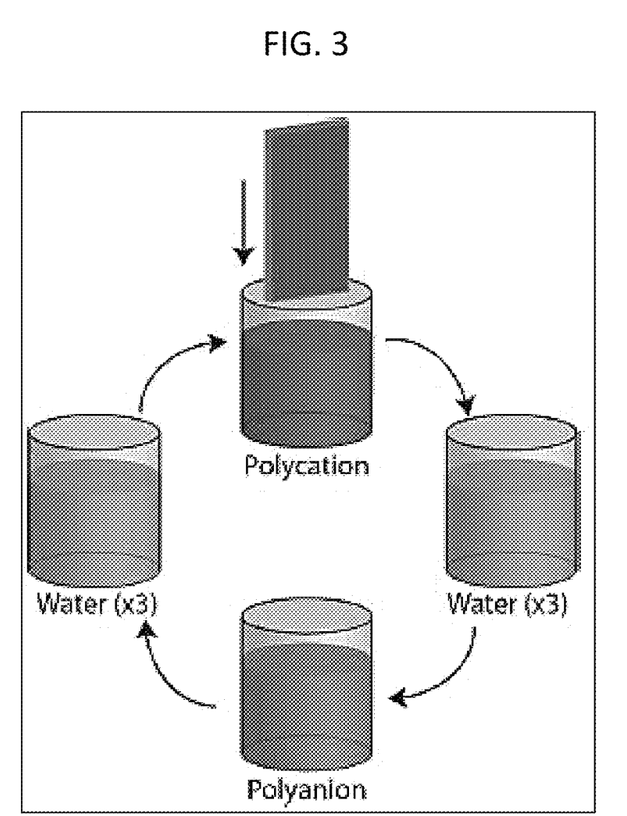
FIG. 3 depicts layer by layer formation of a PEM via dip coating.

In some embodiments, a PEM is formed on the surface by dip coating. In dip coating, the substrate is immersed in a polyelectrolyte solution for a set amount of time (usually 10-15 min), followed by multiple rinses and immersion in a second polyelectrolyte solution of opposite charge. This process is repeated until the desired number of layers is achieved. A scheme of the dip coating process is given in FIG. 3. In some embodiments, dip coating may include immersion in solutions containing drugs, growth factors, and nanoparticles.

In some embodiments, the PEM is formed on the surface by spray coating. In some embodiments, a polyelectrolyte may be sprayed onto the surface for 3-10 sec followed by a rest/draining period of 10-30 sec, washing of the surface with a water spray for 3-20 sec, an additional rest period of 10 sec, and repeating the cycle with a polyelectrolyte of opposite charge. High quality coatings with 20 bilayers of poly (styrene sulfonate)/poly (allylamine hydrochloride) (PSS/PAH) can be prepared in 4 min using spray coating. A comparable dip coated PEM was thicker (65 vs. 45 nm) and required ~17 hr to construct. Spray coating has also been shown to be an effective method of incorporating vesicles within PEMs for controlled release applications.

In some embodiments, the PEM is formed on the surface by spin coating. Spin coating is a highly controlled method for solution-based coating of a system. A typical spin coating procedure includes spin coating for 10-15 sec, rinsing at least once by "spin coating" water for 15-30 sec and repeating the procedure with the oppositely charged polyelectrolyte. The wash step may not be necessary in spin coating.

A method to produce crosslinked polyelectrolyte multilayer films has been described which proves to be stabilized with respect to aggressive media, such as solvents, extreme pH, ionic strength jumps, enzymes and/or phagocytic cells, and can therefore withstand numerous physical, chemical and biological stresses. Crosslinked PEM films are first generated by reacting complementary reactive groups of the PEM surface in the presence of a coupling agent (such as 1-ethyl-3-(3-dimethylaminopropyl) carbodiimide (EDC), and optionally in the presence of N-hydroxysuccinimide compounds), as to form amide bonds between said complementary reactive groups giving rise to a cross-linked PEM film. After the PEM is constructed, charged molecules are trapped by the cross-linked PEM. This method may lead to decreased diffusion rates for the charged molecule moving from the surface to the culture medium. However, protein released from such systems is controlled by the growth factor concentration in the initial solution and also by the cross-link density. Cross-link density ends up being important because limited amounts of protein can diffuse into a highly cross-linked system per unit time.

Controlled Release.

When designing a system for the controlled release of growth factors or charged molecules, there are a number of important parameters to asses. These parameters may, for example, include 1) efficacy—the new technology must be at least as effective as current options; 2) reliability—release of the charged molecule should be controllable and repeatable; 3) durability—shelf life must be sufficient and technology must be able to withstand reasonable pre-implantation/injection handling; and 4) end user approval—minimal/no side effects for patients, and any changes to traditional clinical procedures and/or to cell culture procedures (i.e. GMP/GLP practices for therapeutic cell expansion, cell manufacturing, etc.) should be minimal or simplify protocol (i.e., fewer injections).

Depending on the desired effect and the active charged molecule, different release behaviors can be desired. In some embodiments, the charged molecule is released from the PEM via a burst release, followed by some level of steady state release. Steady state release for several days will maintain the presence and concentration of the growth factor in culture. In contrast, in current culture methods, cell culture medium is exchanged periodically, which can result in fluctuations in growth factor concentrations. Some growth factors are only stable for several hours in culture medium, and need to be added exogenously more than once per day (e.g., FGF-2 addition to maintain proliferation of undifferentiated skeletal muscle progenitor cells). Controlled release surfaces enable controlled, steady release of growth factors to cells without addition of exogenous growth factors. The release behavior is dictated by the release mechanism as well as by the release trigger. Release can be triggered by changes in pH or temperature or by the use of an external field (i.e., magnetic, ultrasonic, or laser-induced release).

Figure 4A:
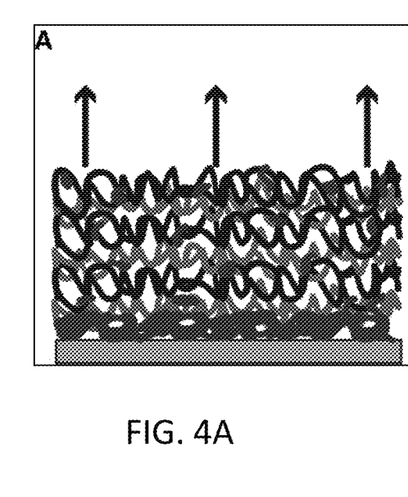
FIGS. 4A, 4B and 4C illustrate diffusion and degradation of charged molecules from a PEM as release mechanisms.
Figure 4B:
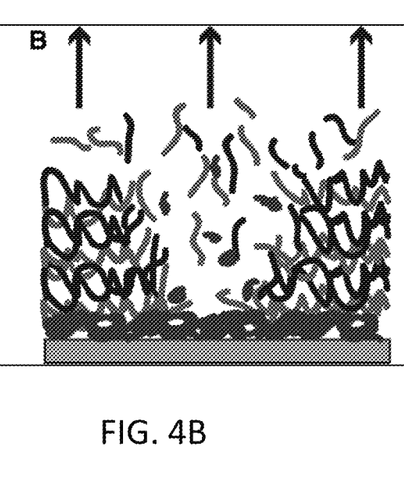
Figure 4C:
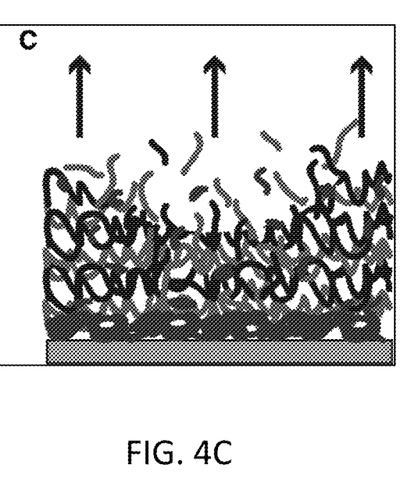

In some embodiments, the release mechanism is diffusion through the delivery material. In some embodiments, the release mechanism is degradation of the delivery material. In some embodiments, both diffusion and degradation mechanisms may be employed. These three release options are shown in FIG. 4A (diffusion) and FIG. 4B (degradation) and FIG. 4C (degradation and diffusion occurring together).

In some embodiments, a method for modulating a release of a charged molecule is provided. In some embodiments, the initial concentration of the charged molecule can be changed to modulate the rate, duration, or both of the charged molecule release. For example, in some embodiments, the initial solution concentration of the charged molecule can be between about 0.025 mg/mL and about 0.1 mg/mL. In some embodiments, the initial solution concentration of the charged molecule can be increased to about 0.1 mg/mL to about 1 mg/ml, or to about 0.1 mg/mL and about 10 mg/mL.

In some embodiments, the release of the charged molecule can be modulated by changing assembly pH, with slower rate of release near the closed state of the complex formed between polyanion and polycation, as described above. For example, in the case of PMAA and PLH, this occurs around pH=6-7. In some embodiments, rapid release can be achieved through the use of a strong polyanion and strong polycation, while more control is achieved when at least one of the polyelectrolytes used is weak.

Removal of Coatings

In some embodiments, the PEM may be removed or stripped so that the culture device may be re-used without the PEM or with different PEM. Polyelectrolyte multilayers prepared in this manner can be fully removed from the surface through cleaning sequentially in 1M NaOH and 1M HCl, followed by rinsing in water. The strong acid and base act to break the electrostatic bonds between the polyelectrolyte multilayer and the substrate surface. Surfaces can then be reused. Since the charged molecules that are being released are biological materials, the charged molecules typically exhibit pH dependent charge states (through a combination of weak/strong charges and zwitterionic character) and complex secondary structure. These materials are the tether to the substrate. When the charge molecules, which respond to pH, are exposed to highly basic and highly acidic environments, the electrostatic bonds and other secondary bonds (maybe hydrogen bonding) between the coating and the substrate are cleaved. Preferred acid/base concentration of 1M to 0.1M may be used.

Examples, which are set forth to aid in the understanding of the disclosure, and should not be construed to limit in any way the scope of the disclosure as defined in the claims which follow thereafter. The following examples are put forth so as to provide those of ordinary skill in the art with a complete disclosure and description of how to make and use the embodiments of the present disclosure, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for.

EXAMPLES

Example 1

Figure 5:
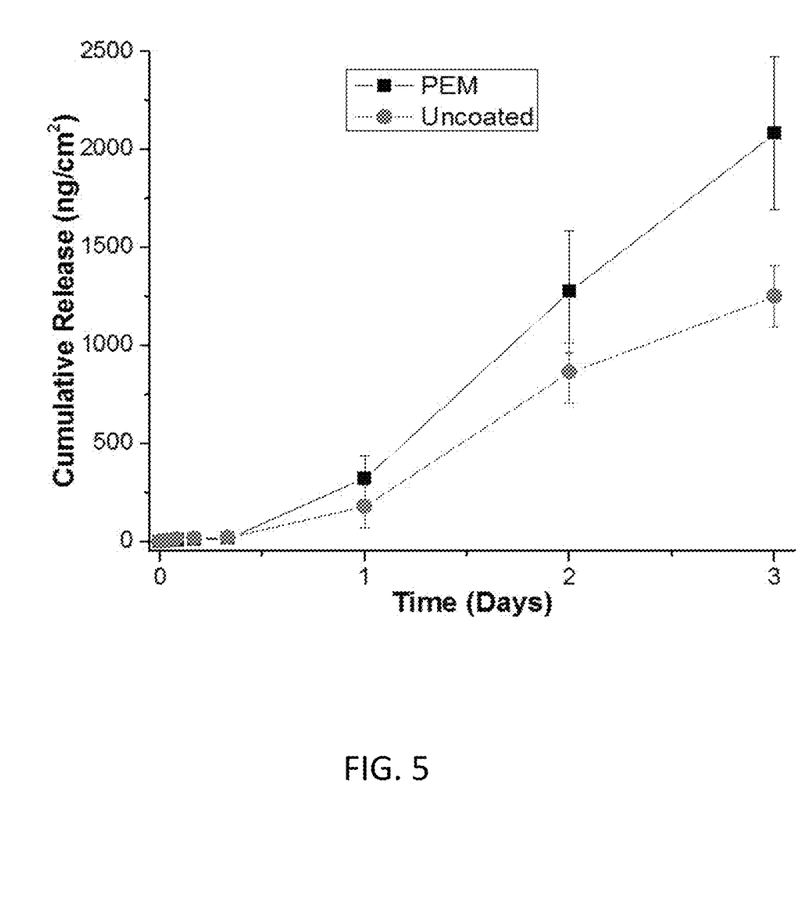
FIG. 5 represents FGF2 release, as measured by ELISA, from fibrin microthreads, either as prepared (uncoated) or coated with a PEM (PEM). In both cases, fibrin microthreads were immersed in a solution containing FGF2. In the PEM case, a PEM was subsequently assembled on the fibrin surface.

PEMs can be assembled on biopolymer substrates such as fibrin microthreads, which are discrete biopolymer fibers, 50-100 μm in diameter, produced from the natural extracellular matrix protein of the provisional matrix FGF2 release is greater from PEM-coated fibrin microthreads as compared to uncoated fibrin microthreads. The same amount of FGF2 was loaded under both conditions, which suggests that the difference in measured FGF2 is due to FGF2's structure being better preserved by PEMs.

FIG. 5 represents FGF2 release, as measured by ELISA, from fibrin microthreads, either as prepared (uncoated) or coated with a PEM (PEM). In both cases, fibrin microthreads were immersed in a solution containing FGF2. In the PEM case, a PEM was subsequently assembled on the fibrin surface.

Example 2

Figure 6:
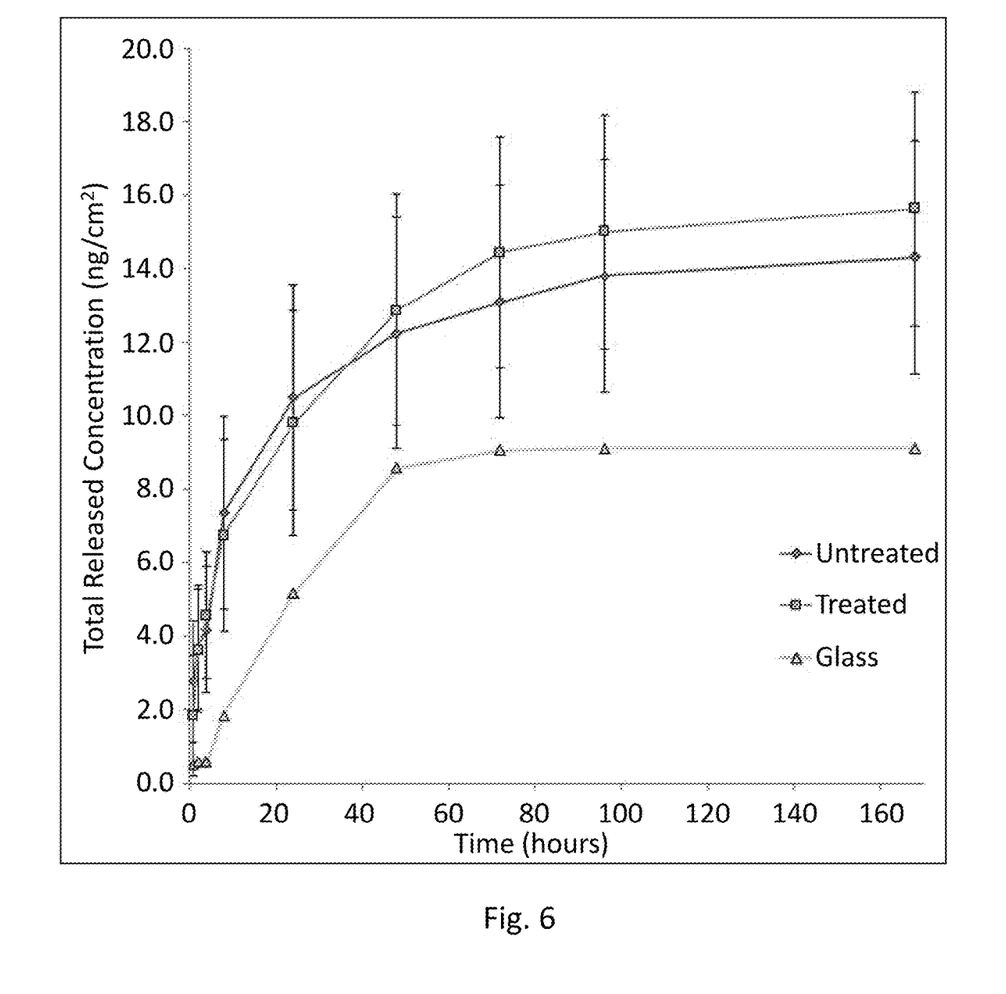
FIG. 6 represents the effect of substrate on FGF2 released over seven days.

FGF2 was adsorbed on different cell culture substrates and a PEM was subsequently assembled on the surface. Untreated polystyrene and tissue culture plastic (treated) exhibit similar release profiles, while less FGF2 is released from the glass surface. The majority of the release is observed in the first 48 hours.

FIG. 6 represents the total amount of FGF2 released over seven days was compared to the amount of FGF2 remaining on the substrate/within the coating. The majority of FGF2 adsorbed to untreated PS remained on the PS surface.

Figure 7:
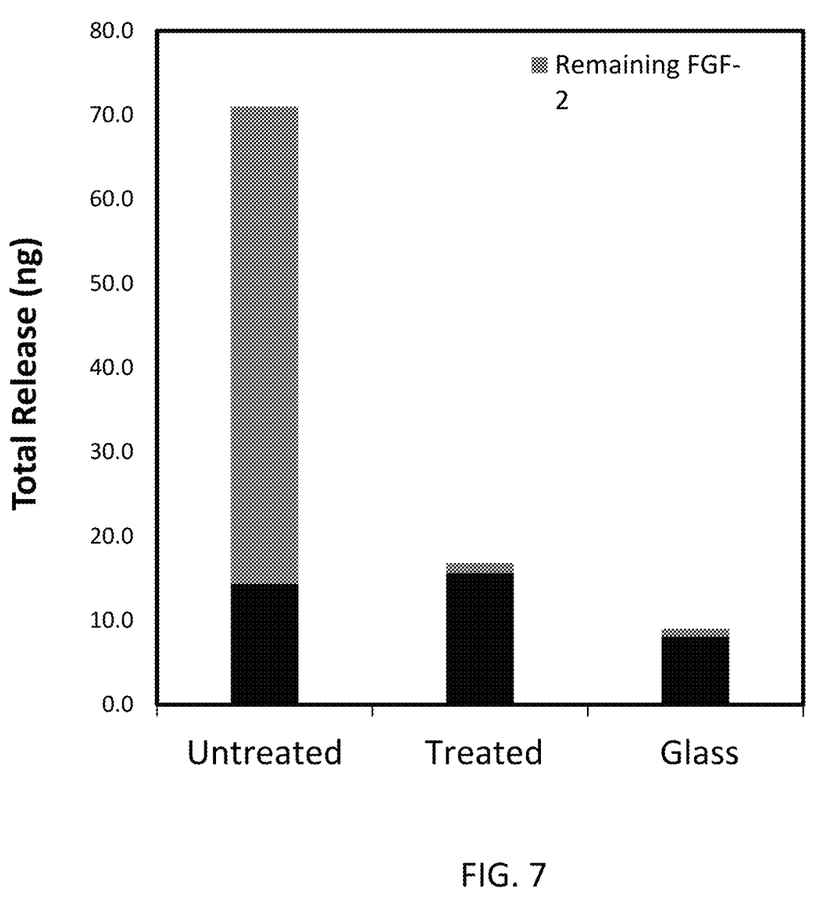
FIG. 7 represents the total amount of FGF2 released over seven days was compared to the amount of FGF2 remaining on the substrate/within the coating. The majority of FGF2 adsorbed to untreated PS remained on the PS surface.

FIG. 7 represents how release can be modulated by adjusting the FGF2 concentration of the initial solution from which FGF2 is adsorbed (substrates are immersed in for 15 minutes). This figure and all subsequent data are for treated PS as the substrate.

Figure 8:
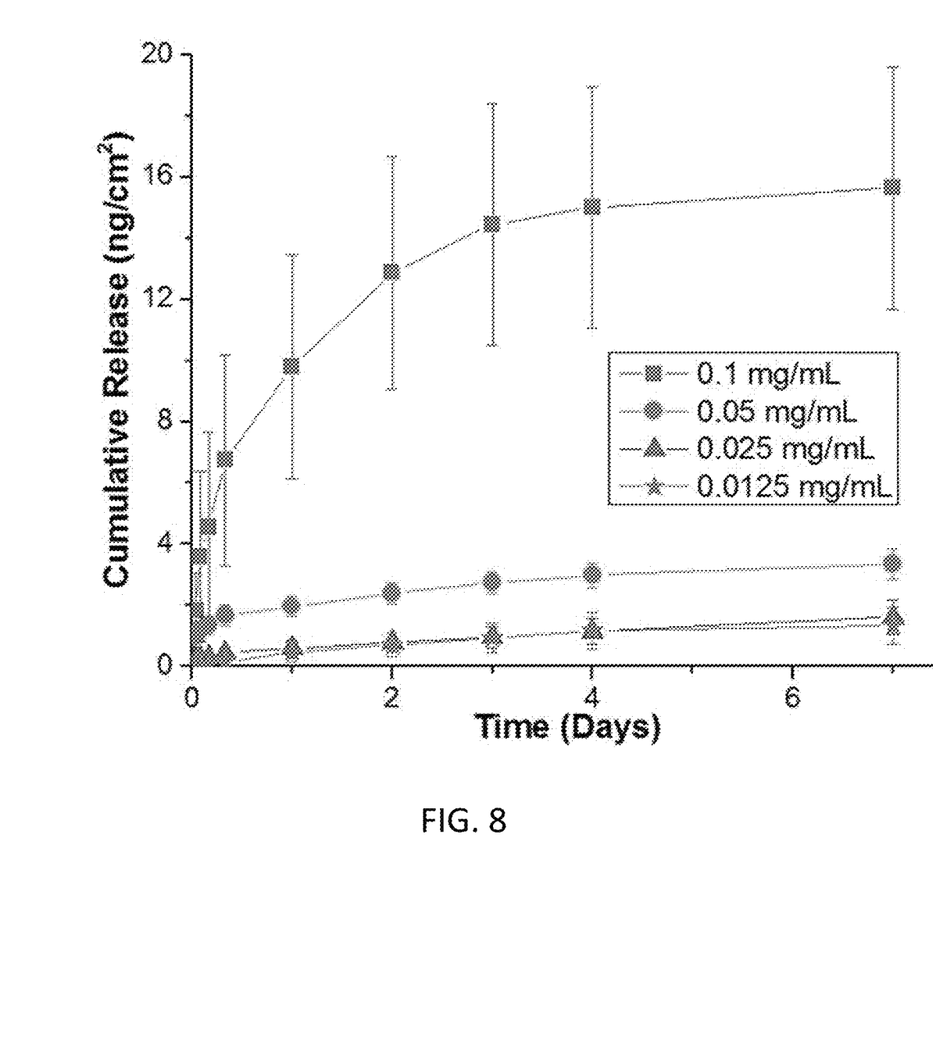
FIG. 8 represents how release can be modulated by adjusting the FGF2 concentration of the initial solution from which FGF2 is adsorbed (substrates are immersed in for 15 minutes) and where this figure is for treated PS as the substrate.

FIG. 8 represents the effect of released FGF2 was compared to bolus addition of FGF2 on CRL-2352 adult human fibroblasts. FGF2 maintains fibroblasts in a proliferative state. BrdU staining was used to identify proliferative fibroblasts. Stained images and the analysis are shown below. The addition of a PEM may reduce the total number of cells; however, the controlled release of FGF2 maintains a similar percentage in a proliferative state as compared to a single addition of FGF2 to the culture medium.

Figure 9:
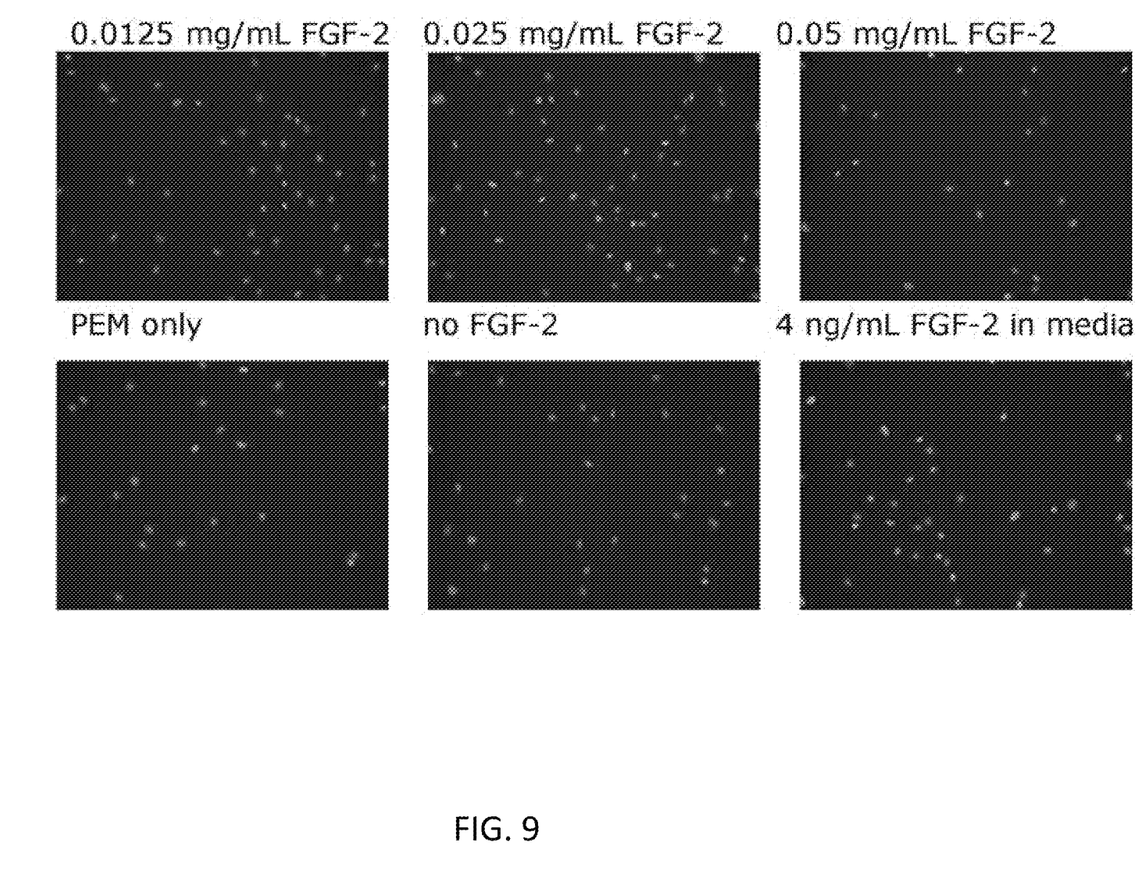
FIG. 9 represents the effect of released FGF2 was compared to bolus addition of FGF2 on CRL-2352 adult human fibroblasts.
Figure 10A:
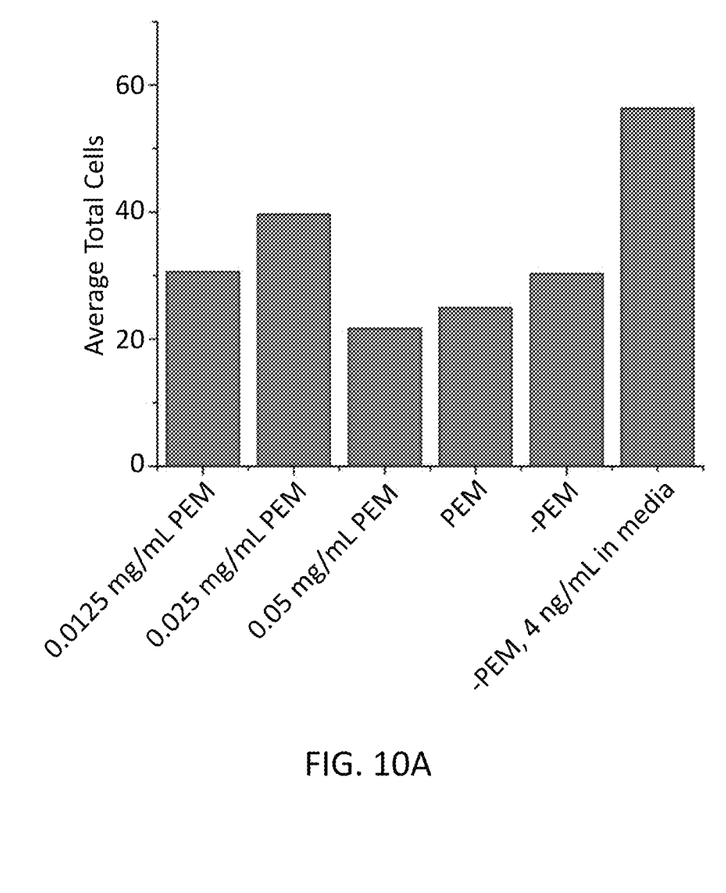
FIG. 10A and FIG. 10B represent analysis of the stained images in FIG. 9.
Figure 10B:
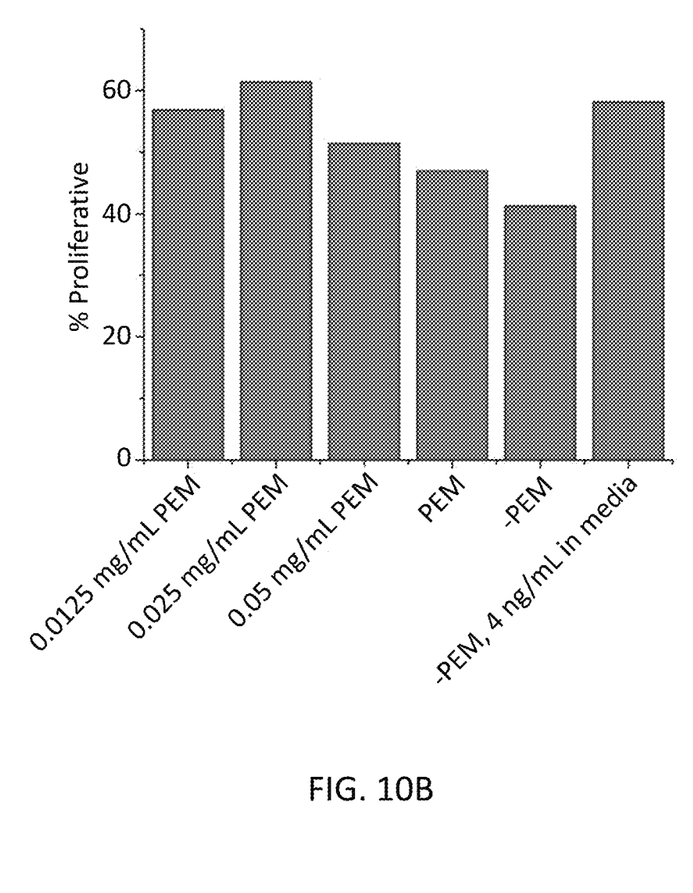

FIG. 9 represents the effect of released FGF2 was compared to bolus addition of FGF2 on CRL-2352 adult human fibroblasts; and FIG. 10A and FIG. 10B represent analysis of the stained images in FIG. 9.

All patents, patent applications, and published references cited herein are hereby incorporated by reference in their entirety. It should be emphasized that the above-described embodiments of the present disclosure are merely possible examples of implementations, merely set forth for a clear understanding of the principles of the disclosure. Many variations and modifications may be made to the above-described embodiment(s) without departing substantially from the spirit and principles of the disclosure. It can be appreciated that several of the above-disclosed and other features and functions, or alternatives thereof, may be desirably combined into many other different systems or applications. All such modifications and variations are intended to be included herein within the scope of this disclosure, as fall within the scope of the appended claims.

What is claimed is:

1. A method of preparing a device for tissue engineering comprising:
    coating at least a portion of a glass or polymer surface of a cell culture device configured for expanding cells in a culture medium with a charged molecule;
    depositing a polyelectrolyte multilayer (PEM) on top of the charged molecule, the PEM comprising 3 to 10 bi-layers of oppositely charged polyelectrolytes, wherein the PEM is a combination of poly(methacrylic acid) (PMAA) and poly-L-histidine (PLH); and
    adjusting, while depositing the PEM, a pH of the polyelectrolytes such that the polyelectrolytes are deposited at the adjusted pH to create the PEM that releases 95% of the charged molecule into the culture medium over 7 days for a concentration of at least 6 ng/cm$^2$ of the released charged molecules in the culture medium between 0 hours and 60 hours of in vitro expansion of the cells.

2. The method of claim 1 wherein the surface is negatively charged or is hydrophilic.

3. The method of claim 2 wherein the charged molecule includes a positively charged portion.

4. The method of claim 1, wherein the pH is adjusted to a pH of 4.

5. The method of claim 1, wherein the charged molecule comprises a growth factor.

6. The method of claim 1, further comprising expanding cells in the culture medium with the charged molecule in the cell culture device.

7. The method of claim 1, further comprising expanding the cells in the culture medium having the concentration of the charged molecule of at least 6 ng/cm$^2$ between 0 hours and 60 hours.

8. The method of claim 1, further comprising identifying an isoelectric point of the charged molecule; and wherein the 3 to 10 bi-layers of the PEM are deposited on top of the charged molecule in an order based on the isoelectric point.

9. The method of claim 8, wherein a first bi-layer layer deposited on top of the charged molecule is a polyanion responsive to identifying that the isoelectric point is greater than 7.

10. The method of claim 8, wherein a first bi-layer layer deposited on top of the charged molecule is a polycation responsive to identifying that the isoelectric point is less than 7.

11. A method of preparing a device for tissue engineering comprising:
   binding a charged molecule on at least a portion of a glass or polymer surface of a cell culture device configured for expanding cells in a culture medium; and
   assembling on the surface, at an adjusted pH level, a polyelectrolyte multilayer (PEM) on top of the charged molecule, the PEM comprising 3 to 10 bi-layers of oppositely charged polyelectrolytes, wherein the PEM is a combination of poly(methacrylic acid) (PMAA) and poly-L-histidine (PLH), wherein the adjusted pH level is adjusted during assembly to create the PEM that releases 95% of the charged molecule into the culture medium over 7 days for a concentration of at least 6 ng/cm$^2$ of the released charged molecules in the culture medium between 0 hours and 60 hours of in vitro expansion of the cells.

12. The method of claim 11 wherein the surface is negatively charged or is hydrophilic.

13. The method of claim 12 wherein the charged molecule includes a positively charged portion.

14. The method of claim 11, wherein the pH is adjusted to a pH of 4.

15. The method of claim 11, wherein the charged molecule comprises a growth factor.

16. The method of claim 11, further comprising expanding cells in the culture medium with the charged molecule in the cell culture device.

17. The method of claim 11, further comprising expanding the cells in the culture medium having the concentration of the charged molecule of at least 6 ng/cm$^2$ between 0 hours and 60 hours.

18. The method of claim 11, further comprising identifying an isoelectric point of the charged molecule; and wherein the 3 to 10 bi-layers of the PEM are deposited on top of the charged molecule in an order based on the isoelectric point.

19. The method of claim 18, wherein a first bi-layer layer deposited on top of the charged molecule is a polyanion responsive to identifying that the isoelectric point is greater than 7.

20. The method of claim 18, wherein a first bi-layer layer deposited on top of the charged molecule is a polycation responsive to identifying that the isoelectric point is less than 7.

* * * * *